United States Patent [19]

Limbach et al.

[11] Patent Number: 4,490,465

[45] Date of Patent: Dec. 25, 1984

[54] COUPLED ENZYME SYSTEMS FOR DETERMINATION OF DISSOLVED SUBSTANCES

[75] Inventors: Berthold Limbach, Seeheim-Jugenheim; Roland Helger, Darmstadt, both of Fed. Rep. of Germany

[73] Assignee: Merck Patent Gesellschaft mit beschränkter Haftung, Darmstadt, Fed. Rep. of Germany

[21] Appl. No.: 478,765

[22] Filed: Mar. 25, 1983

[30] Foreign Application Priority Data

Mar. 26, 1982 [DE] Fed. Rep. of Germany ....... 3211167

[51] Int. Cl.$^3$ .......................... C12Q 1/32; C12Q 1/54
[52] U.S. Cl. ...................................... 435/14; 435/26; 435/805; 435/810
[58] Field of Search ................ 435/14, 26, 25, 4, 805, 435/810

[56] References Cited

U.S. PATENT DOCUMENTS

| | | | |
|---|---|---|---|
| 3,099,605 | 7/1963 | Free | 435/25 X |
| 4,056,442 | 11/1977 | Huang et al. | 435/26 X |
| 4,066,512 | 1/1978 | Lai et al. | 435/14 X |
| 4,120,755 | 10/1978 | Pierre et al. | 435/14 |
| 4,259,440 | 3/1981 | Gupta et al. | 435/805 X |
| 4,340,669 | 7/1982 | Bauer | 435/14 |
| 4,368,261 | 1/1983 | Klase et al. | 435/26 X |

FOREIGN PATENT DOCUMENTS

| | | | |
|---|---|---|---|
| 142973 | 7/1980 | Fed. Rep. of Germany | 435/4 |
| 143180 | 8/1980 | Fed. Rep. of Germany | 435/4 |
| 857874 | 8/1981 | U.S.S.R. | 435/14 |
| 905787 | 2/1982 | U.S.S.R. | 435/4 |

OTHER PUBLICATIONS

Chemical Abstract of Pfeiffer et al., "Glucose Oxidase Bienzyme Electrodes for ATP, NAD+, Starch and Disaccharides", in *Chemical Abstracts,* vol. 94, No. 12373c, 1981.
Abstract of Duine et al., "Glucose Dehydrogenase from Acinetobacter Calcoacetious, a Quinoprotein" in *Chemical Abstracts,* vol. 92, No. 106368, 1980.
Bergmeyer et al., *Principles of Enzymatic Analysis,* NY, Verlag Chemie, 1978, pp. 88–91.
Snoswell, "DL-Lactate Dehydrogenases (NAD+-Independent) from *Lactobacillus arabinasis*", in *Methods in Enzymology:Carbohydrate Metabolism* vol. IX, Ed. by Wood, NY, Academic Press, 1966, pp. 321–327.
Kersters et al., "Primary and Secondary Alcohol Dehydrogenases from Cluconobacter", in *Methods in Enzymology:Carbohydrate Metabolism,* vol. IX, Ed. by Wood, NY, Academic Press, 1966, pp. 350–354.

*Primary Examiner*—Robert J. Warden
*Assistant Examiner*—Randall E. Deck
*Attorney, Agent, or Firm*—Millen & White

[57] ABSTRACT

A test system having an extended range of measurement and a corresponding procedure for the determination of substances in liquids contains several enzymes or enzyme systems together which, independently of one another, react directly or indirectly with the substance to be determined. On adding the test system to the sample solution, various final products are produced which can be distinguished analytically and evaluated by measurement techniques or visually. For example, glucose can be determined over a wide range of concentrations using a combination of an NAD-dependent dehydrogenase and a non-NAD-dependent dehydrogenase.

19 Claims, 4 Drawing Figures

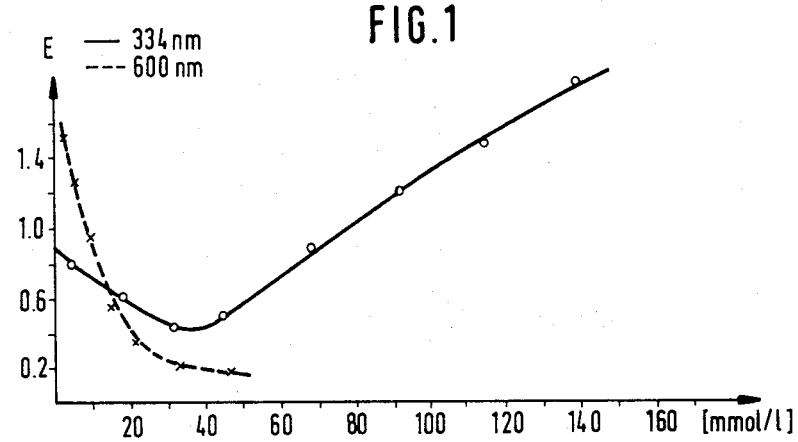
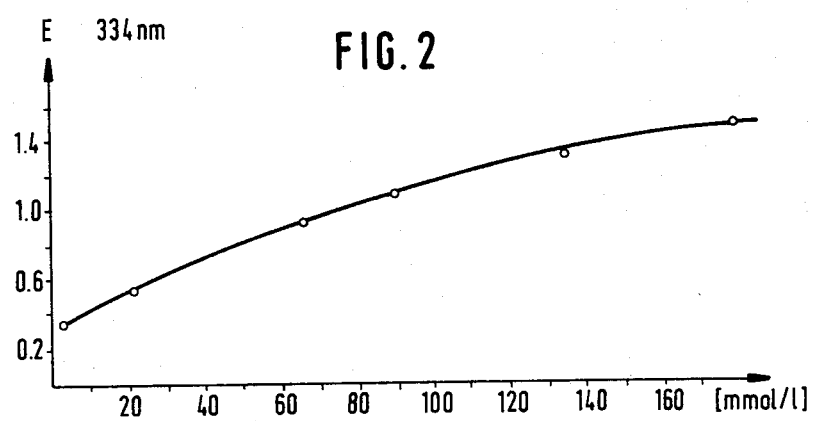

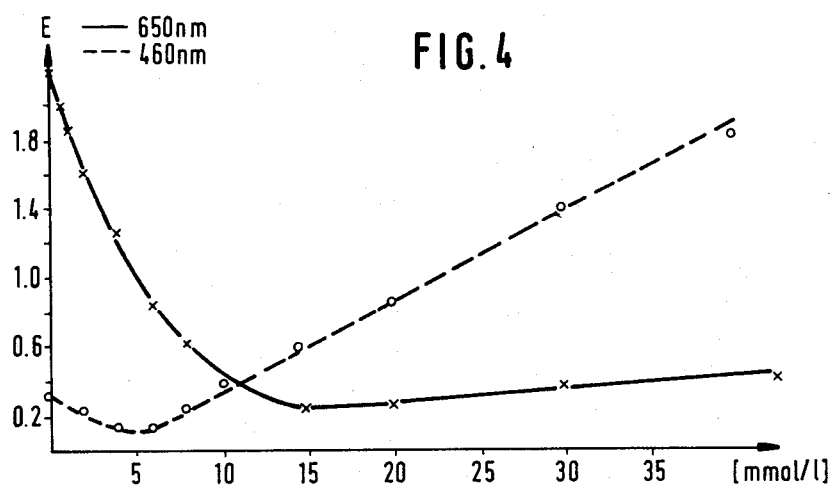

COUPLED ENZYME SYSTEMS FOR DETERMINATION OF DISSOLVED SUBSTANCES

BACKGROUND OF THE INVENTION

This invention relates to a test system and a procedure, using coupled enzyme systems and having an extended range of measurements, for the determination of substances in liquids, in particular in body fluids.

The determination of substances in body fluids is of great importance for medical diagnosis. This applies not only to quantitative determinations, but also to semi-quantitative or qualitative procedures which permit self-monitoring of the individual patient or simple screening. As is appropriate for the importance of these tests, a large number of procedures have been disclosed. The most frequently used procedures are enzymic methods of determination which permit a high degree of specificity. In such methods, the increase or decrease of a reactant participating in the determination reaction is indirectly or directly determined visually, photometrically or using other optical or physicochemical procedures. Common to all these systems is that always only one enzyme or enzyme system reacts with the substance to be determined, whereupon, in an identical or proportional molar ratio, a reaction product is formed or a participant in the reaction is consumed. As a consequence, the range of measurement is approximately equal in size for all procedures, and it can be displaced in accordance with the sensitivity of the measurement signal and the sample dilution.

Tests are necessary for medical diagnosis which are able not only reliably to determine only slightly differing values in the boundary zone between the normal range and the pathological range, but also, at the same time, to cover as wide a range as possible in the pathological range. This also applies, in particular, to screening methods, for example, with test strip systems. The range of measurement achieved with the conventional tests is inadequate for the requirements of some applications. This is particularly true for the determination of glucose. Attempts have already been made to solve this problem by using additives in the tests which change their sensitivity but a wider range of measurement has been achieved heretofore only by using a combination of several tests, each having a range of measurement which is adjusted to be appropriately different from the others.

OBJECTS OF THE INVENTION

One object of the present invention is to provide enzymatic assay compositions permitting determinations of dissolved substrates to be made over a much wider range of measurement than has been made possible heretofore, without loss of accuracy.

Another object of the invention is to provide a method of accurately determining the concentration of a dissolved substrate over a wide range of concentrations, particularly a range which includes both normal and pathological ranges.

Upon further study of the specification and appended claims, further objects and advantages of this invention will become apparent to those skilled in the art.

SUMMARY OF THE INVENTION

The invention relates to a test system with an extended range of measurement for the determination of substances in liquids, which comprises several enzymes or enzyme systems together which, independently of one another, react directly or indirectly with the substance to be determined.

The invention further relates to a method for the determination of substances in liquids, which comprises treating a sample solution simultaneously with several enzymes or enzyme systems which, independently of one another, react directly or indirectly with the substance to be determined, there being produced various final products which can be distinguished analytically and evaluated by measurement techniques or visually.

DETAILED DISCUSSION

Sequential coupling of various enzymatic reactions is known in a large number of examples, such as the hexokinase/glucose-6-phosphate dehydrogenase reaction for the determination of glucose or the urease/glutamate dehydrogenase reaction for the determination of urea. Common to these enzyme systems is that they act consecutively, i.e., the reaction product of the first reaction is the starting substrate for the second reaction.

Parallel coupling of different enzymatic reactions, i.e., the simultaneous presence of several enzyme systems converting the same substrate, ought to lead to competition between the two reactions and thus to interdependence of the reactions. Thus, for example, on coupling the glucose oxidase reaction with the $NAD^+$-dependent glucose dehydrogenase reaction, the two reactions take place simultaneously; the ratio of the final products formed in each reaction depends on the concentration of the two enzymes in each case. If, for example, under conditions which are otherwise identical, the concentration of glucose oxidase is increased, less NADH is produced at the same concentration of glucose. It is true that, by this means, there is an overall widening of the range of measurement, but this is at the expense of the accuracy of measurement. Moreover, both reactions cover a common range of measurement.

Thus, it is all the more surprising that it is possible to couple several enzyme systems which, independently of one another, convert the same substrate directly or indirectly into different products, at least two different signals for measurement being obtained in a reaction mixture, and each of these cover two different ranges of concentration of the substance to be determined. In this context, "independently of one another" signifies that in the simultaneous presence of the systems according to the invention converting the substance, the conversion by the second system only takes place after the coenzyme of the first system has been largely consumed, i.e., generally after conversion of at least about 90%, of the coenzyme. By this means, two defined ranges of measurement are obtained in an overall range of measurement.

The enzymes or enzyme systems according to the invention are preferably dehydrogenases with electron acceptors or donors which are independent of one another. Preferably, the test system comprises the following components:

(a) a pyridine-linked dehydrogenase enzyme or enzyme system, wherein oxidation or reduction of the substrate is coupled with conversion of reduced or oxidized nicotinamide-adenine dinucleotide (NADH, $NAD^+$) or nicotinamide-adenine dinucleotide phosphate (NADPH, $NADP^+$);

(b) a non-pyridine linked dehydrogenase enzyme or enzyme system, which is not coupled with conversion of the pyridine-based coenzymes mentioned under (a), but instead is coupled with conversion of an electron acceptor or donor which provides a signal for measurement distinguishable from these coenzymes. Substances of this type are known, including, e.g., coenzymes belonging to the class of cytochromes, quinones or pyrroloquinoline-quinones; flavin nucleotides, hexacyanoferrate, methylene blue, phenazine methosulfate, phenazine ethosulfate, benzoquinone, dichlorophenol-indophenol, dichloroindophenol, trichloroindophenol and the like are also suitable. Appropriate enzymes converting these coenzymes are known from the literature; and (c) all the coenzymes and auxiliaries necessary for carrying out a diagnostic test using the enzyme system according to the invention, such as buffers, stabilizers, chromogens and the like.

The assay system of the invention can be provided in a variety of forms, including e.g., test kits and test strips.

Typically, a test kit will include two vials with lyophilized test substances. One of the vials contains the two dehydrogenases and diaphorase; the other contains the coenzymes and auxiliaries necessary for carrying out the diagnostic test. A single vial package containing all reagents is also possible. At the time of use, the contents of both vials are dissolved in the test buffer.

Typically, a test strip will be prepared by impregnating an absorbent material with solutions containing the reagents necessary for the corresponding determination. Suitable absorbent carriers for the test strips of the invention include all those inert absorbent carriers customarily in use for such tests. Most widespread is the utilization of filter paper, but other absorbent cellulose or synthetic resin products can likewise be employed.

A test system according to the invention having two defined ranges of measurement, which complement each other to give an extended overall range of measurement, is obtained by coupling one of each of the enzymes or enzyme systems mentioned under (a) and (b). As examples, a selection of substances which can be determined using the test system is compiled in the table below. The numbers given for the NAD-dependent (pyridine-linked) and non-NAD-dependent (non-pyridine linked) enzymes correspond to the enzyme nomenclature of the Nomenclature Committee of the International Union of Biochemistry:

| Test substance to be determined | NAD-dependent enzyme | Non-NAD-dependent enzyme |
|---|---|---|
| Alcohol | 1.1.1.1 | 1.1.99.8 |
| Glucose | 1.1.1.47 | 1.1.99.- |
| Glycerol 3-phosphate | 1.1.1.8 | 1.1.99.5 |
| Glycine | 1.4.1.10 | 1.4.2.1 |
| Lactate | 1.1.1.27 | 1.1.2.3 |
| Malate | 1.1.1.37 | 1.1.99.16 |
| Mannitol | 1.1.1.67 | 1.1.2.2 |

The foregoing table can be extended, as desired, to other substrates and other known pyridine-linked and non-pyridine-linked enzymes.

Suitable such substrates include, generally, substrates having functional groups susceptible to enzyme-catalyzed dehydrogenation or hydrogenation. Examples of such substrates include, but are not limited to alcohols, aldehydes, ketones, amines (especially amino acids), compounds having adjacent carbon-hydrogen bonds potentially removable to form olefins, unsaturated compounds, and the like.

Suitable such enzymes may be found in standard reference compilations, e.g., Boyer, P. D. The Enzymes, Academic Press, New York; Dixon Webb, Enzymes, 3rd Ed., Academic Press, New York, 1979.

In the case of glucose determination, the NAD-dependent enzyme glucose dehydrogenase 1.1.1.47 is preferably from *Bacillus megaterium*, and the non-NAD-dependent enzyme glucose dehydrogenase 1.1.99 is preferably from *Acinetobacter calcoaceticus*. Glucose determinations effected with separate systems which each contain only one (NAD-dependent or non-NAD-dependent) glucose dehydrogenase, at the same sample dilution, are limited to ranges of measurement which are each differently positioned but which each have approximately the same concentration range. In contrast, a coupled system comprising both enzyme systems together makes a significantly wider range of measurement possible without loss of accuracy.

It will be recognized that coupling of glucose dehydrogenase and glucose oxidase also leads to an extension of the range of measurement but, due to the mutual competition, the expected decrease in the accuracy of measurement is also produced.

The enzyme system converting NAD can additionally contain a tetrazolium salt and a system transferring electrons thereto, e.g., diaphorase.

As a rule, the enzymes described directly convert the substance to be determined. However, it is also possible to couple the coupled enzyme system according to the invention with one or more preceding enzyme reactions. The following reaction system may be quoted as an example:

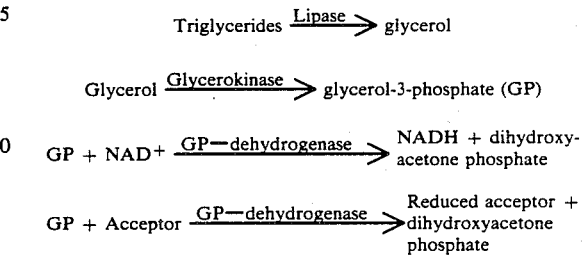

It is possible by this means to carry out test procedures having extended ranges of measurement for a large number of determinations.

The relative amounts of the pyridine-linked dehydrogenase and the non-pyridine-linked dehydrogenase, as well as the coupled electron donors or acceptors, to be used in the composition and method of the invention will be determined by the desired concentration ranges of the substrate to be assayed and by the rate constants for the enzymes.

Likewise, it is possible, using the test system according to the invention, to convert a substrate which is formed in a reaction by conversion of an enzyme to be determined. By this means, in particular, interfering effects, such as additive blank values, can be eliminated in a simple manner. Thus, for example, in the determination of amylase, the endogenous glucose can be removed in a first reaction, while the range of measurement associated with the second reaction is completely retained for the determination of the glucose formed.

The test system according to the invention also makes it possible to change one range of measurement while the second remains unchanged. By this means, the test system according to the invention can be affected in such a manner that a range of measurement exists for the boundary zone covered between the normal range and the pathological range, which corresponds to the conventional methods, while the range of measurement for the pathological range can be variable and adjusted to suit the requirements of medical diagnosis. In the case of glucose determination, this can be achieved, e.g., by the addition of appropriate amounts of glucose oxidase and peroxidase.

The enzymatic determination using the test system according to the invention is effected in the manner customary for enzymatic methods, but both enzyme systems are added simultaneously to the sample solution. The evaluation can be effected visually, photometrically or with other optical or physicochemical methods. In the case of photometric determination, the evaluation can be effected by the end-point procedure at two defined wavelengths (e.g., at 334 and 600 nm or at 460 and 650 nm). The extinction at 334 nm will rise as $NAD^+$ is converted to NADH. Addition of a tetrazolium salt and an associated electron transfer system can be used to couple production of NADH with reduction of the tetrazolium salt, which leads to an increase in the extinction at a wavelength associated with the resultant reduced tetrazole, e.g., at 460 nm when 3-(4-iodophenyl)-2-(4-nitrophenyl)-5-phenyl-2H-tetrazolium chloride (INT) is used. The extinction at, e.g., 600 and-/or 650 nm will fall as dichlorophenol-indophenol is reduced.

It is equally possible to record and evaluate the kinetic course of reaction at one or two wavelengths. Thus, the extended range of measurement principally makes possible a simpler determination of even raised pathological values for a substance; additional dilution is not necessary.

Visualization can be effected by using suitable combinations of known enzymes, coenzymes, dyes and electron transfer systems. Substrate concentrations are determined by, e.g., comparison of the color of a solution or test strip with a reference solution or chart.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Determination of glucose with a coupled system of glucose dehydrogenase/NAD and glucose dehydrogenase/dichlorophenolindophenol 1 ml of each of the following reaction mixtures, which contain (a)
 0.12 mol/liter of phosphate buffer, pH 6.5,
 1.0 mmol/liter of $NAD^+$,
 5.0 kU/liter of glucose dehydrogenase from *Bacillus megaterium*
(b)
 0.12 mol/liter of phosphate buffer, pH 6.5,
 0.12 mmol/liter of dichlorophenol-indophenol,
 250 U/liter of glucose dehydrogenase from *Acinetobacter calcoaceticus* are mixed together and 40 μl of serum (deproteinized 1+1 with 0.3 mol/liter of trichloroacetic acid) having various defined glucose contents are added. The extinction at 334 and 600 nm is measured after 15 minutes in each case. The results obtained are shown in FIG. 1.

FIG. 1 shows that using the system coupled according to the invention, glucose can be determined reliably from 0.5 to more than 160 mmol/liter. 1 mmol/liter corresponds to 18 mg% of glucose. In contrast, with the two individual reactions, in one case glucose determinations can be carried out for 0.5–12 mmol/liter, and in the other case for about 2–60 mmol/liter.

COMPARATIVE EXAMPLE 2

Determination of glucose with glucose dehydrogenase/NAD in the presence of glucose oxidase and peroxidase The conditions of Example 1 and the mixture according to 1(a) are used. The reaction mixture also contains 1 kU/liter of glucose oxidase and 400 U/liter of peroxidase. The measured curve obtained is shown in FIG. 2.

FIG. 2 shows that the coupling of the glucose dehydrogenase and the glucose oxidase reactions again leads to an extension of the range of measurement, but the accuracy of measurement is decreased due to the path of the curve being flattened.

EXAMPLE 3

Visual determination of glucose using a coupled system of glucose dehydrogenase/NAD/diaphorase/tetrazolium salt and glucose dehydrogenase/dichlorophenol-indophenol; alteration of the range of measurement 2 ml of each of four different mixtures, each of which contains 0.12 mol/liter of phosphate buffer, pH 6.5, and $10^{-3}\%$ by weight of sodium fluorescein, are used in a reaction mixture. In addition, the mixtures contain the following Mixture A:
 1 mmol/liter of $NAD^+$,
 0.67 mmol/liter of 3-(4-iodophenyl)-2-(4-nitrophenyl)-5-phenyl-2H-tetrazolium chloride (INT),
 5 kU/liter of glucose dehydrogenase from *B. megaterium* and
 250 U/liter of diaphorase Mixture B 1:
 1 mmol/liter of $NAD^+$,
 0.25 mmol/liter of dichlorophenol-indophenol,
 0.67 mmol/liter of INT,
 2.5 kU/liter of glucose dehydrogenase from *B. megaterium*,
 250 U/liter of glucose dehydrogenase from *A. calcoaceticus* and
 250 U/liter of diaphorase.

Mixture B 2: The reagents detailed in mixture B 1 in the same concentration plus 500 U/liter of glucose oxidase and 200 U/liter of peroxidase Mixture B 3: The reagents detailed in mixture B 1 in the same concentrations plus 1 kU/liter of glucose oxidase and 400 U/liter of peroxidase.

In each case, 60 μl of serum (deproteinized 1+1 with 0.3 mol/liter of trichloroacetic acid) having various defined glucose contents are pipetted into the reaction mixture. After 20 minutes, the color appearance of the total solution is assessed visually; the overall range of measurement corresponds to the range of glucose concentrations which can be distinguished visually. The result is shown as a graph in FIG. 3. The wider range of measurement of the coupled system and the wide variation possible are clearly seen.

EXAMPLE 4

Determination of lactate using a coupled system of lactate dehydrogenase/NAD/diaphorase/tetrazolium salt and lactate dehydrogenase/dichlorophenol-indophenol 2 ml of a reaction mixture are used, which contains
0.25 mol/liter of phosphate buffer, pH 7.0,
1 mmol/liter of $NAD^+$
0.12 mmol/liter of dichlorophenol-indophenol,
0.67 mmol/liter of INT,
5 kU/liter of lactate dehydrogenase from pig heart,
250 U/liter of diaphorase and
200 U/liter of lactate dehydrogenase from yeast
100 μl of serum (deproteinized 1+1 with 0.3 mol/liter of trichloroacetic acid) are pipetted into this. The extinction at 460 and 650 nm is measured after 30 minutes in each case. The results obtained are shown in FIG. 4.

Whereas, using the two single reactions, in one case lactate determinations for 0.2–6 mmol/liter, and in the other case for about 0.8–24 mmol/liter, can be carried out, FIG. 4 shows that, using the coupled system according to the invention, lactate can be determined from 0.2 to more than 60 mmol/liter.

EXAMPLE 5

Determination of alcohol using a coupled system of alcohol dehydrogenase/NAD/diaphorase/tetrazolium salt and alcohol dehydrogenase/dichlorophenol-indophenol 2 ml of a reaction mixture are used which contains
0.3 mol/liter of tris(hydroxymethyl)aminomethane buffer, pH 8.0,
1 mmol/liter of $NAD^+$,
0.12 mmol/liter of dichlorophenol-indophenol,
0.67 mmol/liter of INT,
2 kU/liter of alcohol dehydrogenase (ADH) from yeast,
250 U/liter of diaphorase and
250 U/liter of ADH from Pseudomonas sp. M 27.
50 μl of serum (deproteinized 1+1 with 0.3 mol/liter of trichloroacetic acid) having various defined alcohol contents are pipetted into this. The extinction at 460 and 650 nm is measured after 30 minutes in each case. The range of measurement corresponds to from 0.02 to more than 3 g/liter of alcohol, whereas, using the two single reactions, only ranges of measurement for 0.02 to 0.5 and for 0.08 to 2.2 g/liter of alcohol can be obtained.

EXAMPLE 6

Determination of glucose in urine using test strips

An absorbent material is impregnated with solutions according to Example 3, but with a 20-fold higher enzyme concentration, carefully dried and fixed on a suitable support material. After immersion in the sample solution, e.g., a suitably prepared urine sample depending on the glucose content, color changes are obtained ranging from blue, through blue-green, green, light green, beige, orange and red, to dark red. Glucose concentrations can be determined by comparison with a suitable standard color scale.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for determining the amount of a substrate in solution, said substrate being capable of direct or indirect conversion catalyzed by a dehydrogenase, comprising the steps of:
    (a) admixing a liquid sample containing said substrate with an enzymatic assay system comprising at least a first and second enzyme, to produce an assay solution; wherein each of said enzymes is independently capable of catalyzing the direct or indirect conversion of said substrate, said conversion in each case resulting in production of a product capable of separate direct or indirect analytical measurement or visualization; and wherein said first enzyme is a non-pyridine-linked dehydrogenase which catalyzes conversion and resultant production of a first detectable product over a first detection range, and said second enzyme is a pyridine-linked dehydrogenase which catalyzes conversion and resultant production of a second detectable product over a second, different detection range; and
    (b) directly or indirectly measuring or visualizing said detectable products in said assay solution.

2. The method of claim 1, wherein said assay system further comprises a first electron donor or acceptor which is oxidized or reduced concomitant with conversion by said non-pyridine-linked dehydrogenase, and a second electron donor or acceptor which is oxidized or reduced concomitant with conversion by said pyridine-linked dehydrogenase; and wherein said second electron donor or acceptor is reduced or oxidized nicotinamide-adenine dinucleotide (NADH or $NAD^+$) or nicotinamide-adenine dinucleotide phosphate (NADPH or $NADP^+$).

3. The method of claim 2, wherein said first electron donor or acceptor is the reduced or oxidized form of a cytochrome, a quinone, a pyrroloquinoline-quinone, a flavin nucleotide, hexacyanoferrate, methylene blue, phenazine methosulfate, phenazine ethosulfate, benzoquinone, dichlorophenol-indophenol, dichloroindophenol or trichloroindophenol.

4. The method of claim 2, wherein said substrate is alcohol, glucose, glycerol-3-phosphate, glycine, lactate, malate or mannitol.

5. The method of claim 1, wherein said substrate is converted to an intermediate which is then directly converted in the reaction resulting in production of said product.

6. The method of claim 5, wherein said substrate is at least one triglyceride, and said intermediate is glycerol-3-phosphate.

7. An enzymatic assay reagent system for determining the amount of a substrate in solution, said substrate being capable of direct or indirect conversion catalyzed by a dehydrogenase, comprising an admixture of at least two enzymes, each of which is independently capable of catalyzing the direct or indirect conversion of said substrate, said conversion in each case resulting in production of a product capable of separate direct or indirect analytical measurement or visualization; wherein said first enzyme is a non-pyridine-linked dehydrogenase which catalyzes conversion and resultant production of a first detectable product over a first detection range, and said second enzyme is a pyridine-linked dehydrogenase which catalyzes conversion and resultant production of a second detectable product over a second, different detection range.

8. The assay reagent system of claim 7, which further comprises a first electron donor or acceptor which is oxidized or reduced concomitant with conversion by said non-pyridine-linked dehydrogenase, and a second electron donor or acceptor which is oxidized or reduced concomitant with conversion by said pyridine-linked dehydrogenase; and wherein said second electron donor or acceptor is reduced or oxidized nicotinamide-adenine dinucleotide (NADH or NAD+) or nicotinamide-adenine dinucleotide phosphate (NADPH or NADP+).

9. The assay reagent system of claim 8, wherein said first electron donor or acceptor is the reduced or oxidized form of a cytochrome, a quinone, a pyrroloquinoline-quinone, a flavin nucleotide, hexacyanoferrate, methylene blue, phenazine methosulfate, phenazine ethosulfate, benzoquinone, dichlorophenol-indophenol, dichloroindophenol or trichloroindophenol.

10. The assay reagent system of claim 8, wherein said dehydrogenases are capable of converting alcohol, glucose, glycerol-3-phosphate, glycine, lactate, malate or mannitol.

11. The assay reagent system of claim 10, wherein said second enzyme is a pyridine-linked lactate dehydrogenase; and said first enzyme is a non-pyridine-linked lactate dehydrogenase.

12. The assay reagent system of claim 8, wherein said second enzyme is a pyridine-linked glucose dehydrogenase from *Bacillus megaterium;* and said first enzyme is a non-pyridine-linked glucose dehydrogenase from *Acinetobacter calcoaceticus.*

13. The assay reagent system of claim 12, wherein said second enzyme is a pyridine-linked alcohol dehydrogenase; and said first enzyme is a non-pyridine-linked alcohol dehydrogenase.

14. The assay reagent system of claim 8, wherein said first electron acceptor is dichlorophenol-indophenol.

15. The assay reagent system of claim 8, which further comprises a tetrazolium salt and a system for transferring electrons thereto.

16. The assay reagent system of claim 8, which further comprises glucose oxidase and peroxidase.

17. In a kit for use in an enzymatic assay to determine the amount of a substrate in solution, said substrate being capable of direct or indirect conversion catalyzed by a dehydrogenase, said kit comprising an assay reagent system comprising at least one enzyme for converting said substrate, together with coenzymes and auxiliaries necessary for carrying out an enzymatic assay using said assay reagent system, and at least one container for preparing an assay solution, the improvement wherein said assay reagent system comprises an admixture of at least two enzymes, each of which is independently capable of catalyzing the direct or indirect conversion of said substrate, said conversion in each case resulting in production of a product capable of separate direct or indirect analytical measurement or visualization; wherein said first enzyme is a non-pyridine-linked dehydrogenase which catalyzes conversion and resultant production of a first detectable product over a first detection range, and said second enzyme is a pyridine-linked dehydrogenase which catalyzes conversion and resultant production of a second detectable product over a second, different detection range.

18. The kit of claim 17, wherein said assay system further comprises diaphorase.

19. In a test strip for use in an enzymatic assay to determine the amount of a substrate in solution, said substrate being capable of direct or indirect conversion catalyzed by a dehydrogenase, said test strip comprising an absorbent material impregnated with a solution of an enzymatic assay reagent system for said substrate, together with coenzymes and auxiliaries necessary for carrying out said assay and visualizing the result, the improvement wherein said assay reagent system comprises an admixture of at least two enzymes, each of which is independently capable of catalyzing the direct or indirect conversion of said substrate, said conversion in each case resulting in production of a product capable of separate direct or indirect analytical measurement or visualization; wherein said first enzyme is a non-pyridine-linked dehydrogenase which catalyzes conversion and resultant production of a first detectable product over a first detection range, and second enzyme is a pyridine-linked dehydrogenase which catalyzes conversion and resultant production of a second detectable product over a second, different detection range.

* * * * *